United States Patent [19]

Brilliant

[11] Patent Number: 4,592,726
[45] Date of Patent: Jun. 3, 1986

[54] DIAGNOSTIC MIRROR AND LIGHT FILTER

[76] Inventor: Herbert Brilliant, 2008 Walnut St., Philadelphia, Pa. 19103

[21] Appl. No.: 629,449

[22] Filed: Jul. 10, 1984

Related U.S. Application Data

[63] Continuation-in-part of Ser. No. 455,260, Jan. 3, 1983, abandoned.

[51] Int. Cl.[4] .............................................. A61C 3/00
[52] U.S. Cl. ........................................ 433/31; 433/30; 350/1.1
[58] Field of Search ....................... 433/30, 31; 128/10, 128/11, 21, 22, 23; 350/1.1, 1.5, 1.6, 1.7, 288, 290, 291, 311; 362/140, 141, 260, 293, 804; 250/458.1, 459.1, 462.1

[56] References Cited

U.S. PATENT DOCUMENTS

| | | | |
|---|---|---|---|
| 657,199 | 9/1900 | Lawton | 128/11 |
| 1,589,576 | 6/1926 | Thompson | 128/11 |
| 1,604,873 | 10/1926 | Barnhart | 433/31 |
| 2,563,473 | 8/1951 | Levinson | 350/291 |
| 3,209,192 | 9/1965 | Decker | 350/291 |
| 3,711,700 | 1/1973 | Westlund et al. | 362/804 |
| 3,950,649 | 4/1976 | Yonekubo | 250/458.1 |
| 4,040,727 | 8/1977 | Ketchpel | 350/288 |
| 4,184,196 | 1/1980 | Moret et al. | 433/31 |
| 4,195,329 | 3/1980 | Woog | 362/804 |
| 4,199,686 | 4/1980 | Brunsting et al. | 250/459.1 |

*Primary Examiner*—John J. Wilson
*Attorney, Agent, or Firm*—Howard I. Forman

[57] ABSTRACT

A device is provided for a user to self-diagnose areas of the human body when those areas are treated with a disclosing material which is invisible to the naked eye, but which fluoresces when subjected to appropriately filtered light. In particular the device provides mirror and light-filtering portions such that the user may diagnose areas of his or her oral cavity when treated with and differentiated by the disclosing fluorescent material.

5 Claims, 3 Drawing Figures

DIAGNOSTIC MIRROR AND LIGHT FILTER

This is a continuation-in-part of Application Ser. No. 06/455,260 filed on Jan. 3, 1983 by the same applicant and bearing the same title now abandoned.

CROSS-REFERENCE TO RELATED PRIOR ART

| U.S. Pat. No. | Date | Patentee(s) |
| --- | --- | --- |
| 657,199 | 9/1900 | Lawton |
| 1,589,576 | 6/1926 | Thompson |
| 1,604,873 | 10/1926 | Barnhart |
| 2,563,473 | 8/1951 | Levinson |
| 3,209,192 | 9/1965 | Decker |
| 3,309,274 | 3/1967 | Brilliant |
| 3,711,700 | 1/1973 | Westlund, et al |
| 3,950,649 | 4/1976 | Yonekubo |
| 4,040,727 | 8/1977 | Ketchpel |
| 4,184,196 | 1/1980 | Moret, et al |
| 4,195,329 | 3/1980 | Woog |
| 4,199,686 | 4/1980 | Brunsting, et al |

BACKGROUND AND SUMMARY OF THE INVENTION

This invention relates to a device for use with a fluorescent material, such as a fluorescent dye, so that upon application of the fluorescent material to selected areas of the body, the device of the instant invention may be used to cast filtered light directed through the device upon those areas, whereby to cause the dye or other fluorescent material to fluoresce and differentiate diseased and healthy portions of the area, while also providing a mirror for the user to view those portions. Particular applications of the instant invention are in the areas of dental diagnosis and dental hygiene, such that one may selfdiagnose the oral cavity for lesions, and for foreign matter such as bacterial plaque, microcosms, tartar materia alba and the like.

As indicated in the above-referenced U.S. Pat. No. 3,309,274, an appropriate dye or disclosing material (in the form of solution, paste, powder, or the like) for use with the instant invention, contains a normally-invisible constituent that fluoresces and becomes easily visible when activated by a proper light source. The disclosures of this patent are hereby incorporated herein by reference.

In order to provide light of the proper wavelength range, the device of the instant invention incorporates a light-filtering portion in combination with a reflecting-surface portion, so that the device may be used with a high-intensity beam of light from a generally conventional light source, such as typically found in a dental operatory room, to fluoresce the disclosing dye solution or other fluorescent material, and to make readily visible to the user a sharp delineation between healthy and diseased portions of the area treated by the fluorescent material.

In some areas of the human body, when the fluorescent material is applied and properly illuminated, skin lesions and the like are differentially identified by virtue of the fact that the healthy tissues surrounding the diseased areas are caused to glow, while in other areas of the human body the diseased portions of these areas are caused to glow rather than the healthy portions. The reasons why the fluorescent materials will associate with only diseased areas in the one instance, and with only healthy areas in other cases, are not known. However, and in any event, the diseased or adulterated areas are sharply differentiated by such a fluorescent material. Through the use of the device of the instant invention, such a differentiation between healthy and diseased portions of a treated area, particularly an area of the oral cavity, may be made by the user with respect to his or her own person. The degree of fluorescence exhibited will vary with the types of fluorescent material, light source, and light filter which are employed for the purpose.

Sources of light suitable for providing the focused beam of light with which the device is to be employed range from the common incandescent and fluorescent lamps to the quartz or mercury vapor types, and include the hydrogen bulb which is filled with argon. The high-intensity examination light typically found and used in the conventional dental operatory room is a particularly suitable light source for use with the device of the instant invention. Various color filters or diffraction-type filters may be used to convert any of the various light-beam sources to the proper wavelength of light which will excite and flouresce the specific dye or other fluorescent material chosen. The wavelength range for light which will excite and fluoresce the dye or other fluorescent material will depend upon the particular fluorescent material employed, and can be readily determined from published literature sources. Besides its ability to cause excitation or fluorescence of the fluorescent disclosing solution or other fluorescent material employed, the only other requirement of the filtered light is that its wavelength not mask the fluorescent material's fluorescence with its own color. In other words, the filtered light must be capable of exciting the fluorescent material to cause it to glow, while avoiding masking that material's fluorescence. This can be accomplished by means of selective and substantial filtration of any unreactive wavelengths of light.

When selecting a suitable color filter, i.e., a filter through which will pass only light which will excite a particular fluorescent material or dye, almost any transparent of translucent substance may be used, such as, for example, the more or less flexible films made and sold by the E. I. duPont de Nemours and Company under the trademark, "MYLAR", and the rigid "PLEXIGLAS" acrylic sheets made and sold by Rohm and Haas Company. Even colored glass may be employed in certain instances. In one particular application of the device of the instant invention, a user can positively determine and treat teeth and mouth hygiene problems in the nature of plaque deposits or the like, and can brush his teeth and rinse his mouth while observing, first-hand, the results thereof.

DETAILED DESCRIPTION OF THE INVENTION

Figure 1:
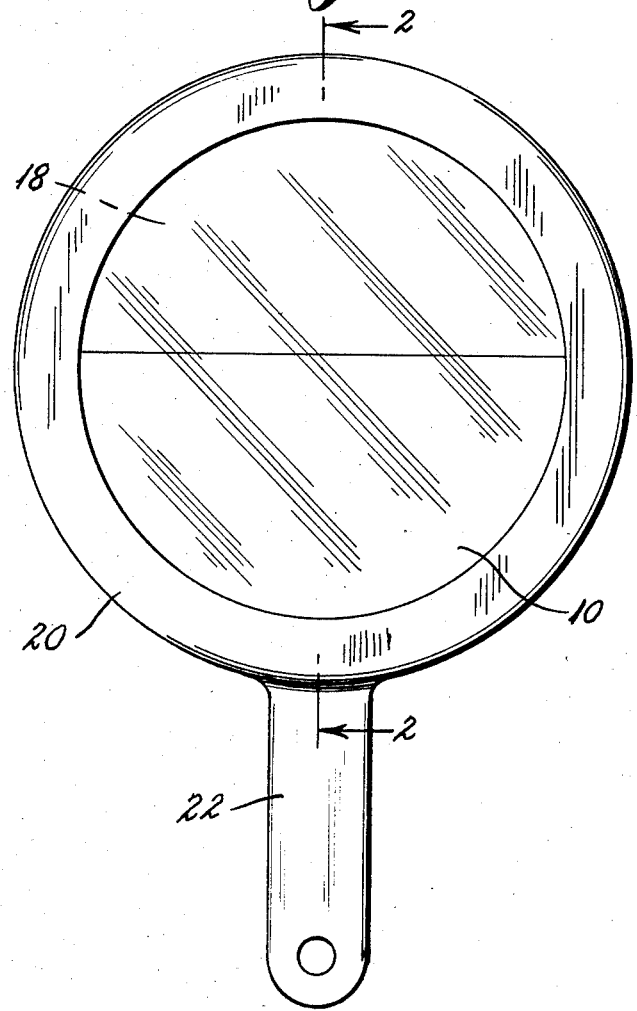
FIG. 1 is a front elevation of one, preferred embodiment of the instant invention.
Figure 2:
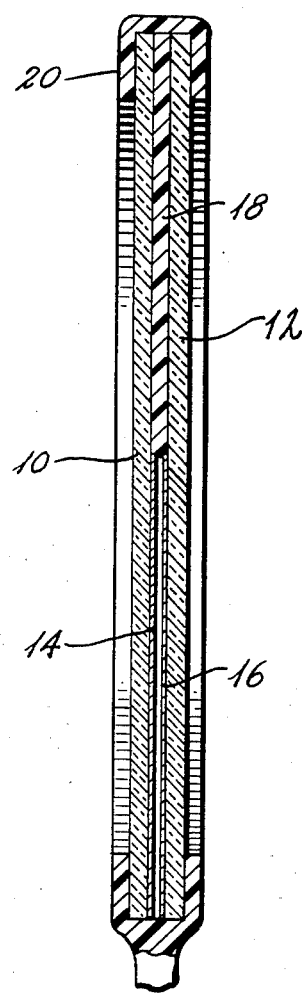
FIG. 2 is a partial, cross-sectional view of the device of FIG. 1, as viewed in the direction of arrows 2—2.

FIGS. 1 and 2 illustrate a combination mirror and light filter supported by a frame 20 having handle 22. Frame 20 and handle 22 conveniently can be fabricated from a rigid material such as plastic or wood. Transparent members 10 and 12, fabricated from a material such as glass, plastic or the like, are mounted in opposed but separated corresponding positions within frame 20, and corresponding lower portions of their inner surfaces are each coated or otherwise provided with reflective means 14 and 16, conveniently consisting of the coventional reflective silver coating material typically employed in the construction of a mirror, in order that a portion of each external surface of the device will act as a mirror. In the remaining portions, i.e., the upper portions, of the inner surfaces, of transparent members 10 and 12, the reflective material has been omitted or removed and a light-filtering material 18, coveniently consisting of a thin, bluish film of "MYLAR" material, has been inserted therebetween so that these portions allow light to enter from either side of the device and to exit from the other side as filtered light. Additionally, one or both of the mirror portions 14 and 16 of the device may be adapted to magnify as well as reflect images incident thereon.

Figure 3:
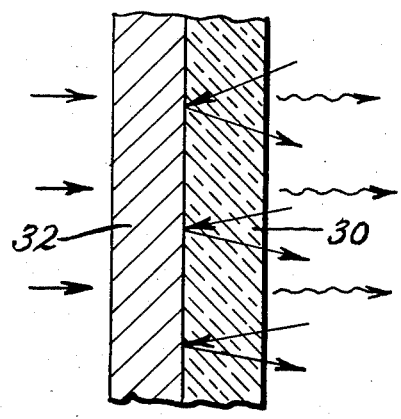
FIG. 3 is a partial, cross-sectional view of an alternate embodiment of the instant invention.

Referring to FIG. 3, an alternate embodiment of the instant invention comprises transparent material 30, such as plastic, glass or the like, and a layer 32 which is coated on or otherwise applied to one side of transparent member 30 such that, as viewed in FIG. 3, light which is incident upon layer 32 is passed therethrough and exists as filtered light, whereas light incident upon layer 32 from the other side is reflected therefrom.

As a simple method of manufacture of the device of FIGS. 1 and 2, two conventional mirrors may have their reflective coating removed from corresponding portions thereof and a light-filtering member may be sandwiched between the two mirrors such that light passing through these portions of the mirrors which had their reflective coatings removed will filter light of a particular portion of the light spectrum.

A possibly preferred method of manufacture of the device would be to start with a transparent optical blank made of glass or plastic, cover a portion of the blank's surface with a substantially non-porous material such as metal, ceramic, wood, paper, wax or another piece of glass or plastic, and then apply to the blank's non-covered portion a reflecting coating of silver or aluminum. If desired, a ¼ wave length coating of magnesium fluoride can be superimposed over the reflecting coating to harden the silver or aluminum in situ. Such coatings can conveniently be applied by any of a number of conventional means such as vacuum or electro-deposition techniques, spraying, dipping in baths of the coating material, et al.

After the reflecting coating is applied the covering material could be removed and it or another cover can be positioned over the reflecting surface to prevent any additional reflecting material from depositing on that surface. A suitable light-filtering substance then is applied to a portion of the blank's surface which is devoid of the reflecting material, thereby enabling that blank portion to filter light of a particular portion of the light spectrum.

Another option is to use more than one glass or plastic optical blank, for example two of glass, or two of plastic, or one of each of glass and of plastic. In a two-membered construction one member can be coated with a reflecting substance, and the other member can be coated with a light filtering substance. The two such coated members are then placed in a uni-planar relationship, preferably in a contiguous juxtaposition similar to that depicted in the drawings by the elements identified by reference characters 10 and 18, and maintained in that position by a suitable frame or holder such as is represented by reference character 20.

In use, a person may support and minipulate the device between himself and a light source such that light filtered through the filtering portion of the device is focused on a particular area of the body, e.g., the oral cavity, and a reflection of the oral cavity may be viewed by the user in the mirror portion of the device. This is particularly useful when areas of the oral cavity have been treated by a fluorescent dye or other suitable fluorescent material as disclosed in U.S. Pat. No. 3,309,274, such that diseased and healthy portions of the area are readily differentiated by impingement of the filtered light into the dye field to cause the dye to fluoresce. It thus can be seen that the reflecting and light-filtering portions of the device cooperate so as to permit the simultaneous delineation and observation by the user of foreign matter, such as plaque, or other undesirable conditions on his or her own person, including his or her own oral cavity.

It thus will be seen that the objects set forth above, including those made apparent from the preceding description, are efficiently attained.

Modifications to the device of the instant invention will be readily apparent to those skilled in the arts. Since these and other changes may be made in carrying out the above method, and in the constructions specifically set forth herein, without departing from the scope of the invention, it is intended that all matter contained in the above description or shown in the accompanying drawings shall be interpreted as illustrative and not in a limiting sense.

It also is to be understood that the following claims are intended to cover all of the generic and specific features of the invention herein described, and all statements on the scope of the invention which, as a matter of language, might be said to fall therebetween.

The invention claimed is:

1. A non-electrified optical handpiece for viewing an area of the user's body which has been treated with a dye or other material that fluoresces when subjected to appropriately filtered light, whereby the fluorescent material when illuminated improves differentiation between diseased and healthy portions of said area, said optical handpiece consisting essentially of:
    (a) a single unitary substantially uni-planar optical member having a surface of which a portion is at least partially mirrored so as to be capable of reflecting light from a source remote from said handpiece, and another portion of which is at least partially transparent so as to be capable of transmitting said light, and
    (b) a light filtering material covering at least a portion of said optical member's transparent portion for filtering said light and providing a filtered light sufficient to fluoresce said fluorescent material.

2. The optical handpiece of claim 1 in which the uni-planar optical member consists of two elements, one having the surface of which a portion is at least partially mirrored and the other having the portion which is at least partially transparent.

3. The optical handpiece of claim 1, the mirrored surface being capable of magnifying at least a portion of the reflected image viewable by the user.

4. A method of manufacturing a dental aid for viewing diseased and healthy areas of a user's cavity when said areas have been treated with a fluorescent material which fluoresces when subjected to appropriately filtered light, such that said user may differentiate between healthy and diseased areas, comprising the steps of:
  (a) partially shielding a transparent, uni-planar optical member by means of a removable cover so that upon deposition of a reflecting material on a surface thereof only the non-shielded portion of that surface will have light reflecting capability,
  (b) depositing a light reflecting material on the non-shielded portion of said optical member,
  (c) removing the cover so as to leave exposed the portion of the optical member which has been shielded by the cover, and
  (d) applying a light filtering material to the previously shielded, exposed portion of the optical member's surface which will be able to filter said light and provide a filtered light capable of fluorescing said fluorescent material.

5. A method of manufacturing a dental aid for viewing diseased and healthy areas of a user's oral cavity when said areas have been treated with a fluorescent material which fluoresces when subjected to properly filtered light, such that said user may differentiate between healthy and diseased areas, comprising the steps of:
  (a) removing a reflective material from a portion of a mirror to allow passage of light therethrough, and
  (b) applying a light-filtering material to said portion to filter said light and provide a filtered light sufficient to fluoresce said fluorescent material.

* * * * *